(12) United States Patent
Grabek

(10) Patent No.: US 6,666,861 B1
(45) Date of Patent: Dec. 23, 2003

(54) ATRIAL APPENDAGE REMODELING DEVICE AND METHOD

(76) Inventor: James R. Grabek, 416 River St., Minneapolis, MN (US) 55401

( * ) Notice: Subject to any disclaimer, the term of this patent is extended or adjusted under 35 U.S.C. 154(b) by 37 days.

(21) Appl. No.: 09/679,968

(22) Filed: Oct. 5, 2000

(51) Int. Cl.[7] ............................................. A61B 18/18
(52) U.S. Cl. ........................... 606/41; 606/46; 606/48; 606/108; 606/111; 606/113; 606/159; 600/16; 600/101; 604/21; 604/22
(58) Field of Search ..................... 606/1, 111, 113, 606/7, 10, 13, 41, 45, 46, 108, 159, 205; 600/16, 101; 604/51–53, 21, 22; 128/898

(56) References Cited

U.S. PATENT DOCUMENTS

| 5,306,234 | A | * | 4/1994 | Johnson ....................... 128/898 |
| 5,984,917 | A | * | 11/1999 | Fleischman et al. ........ 606/139 |
| 6,488,689 | B1 | | 12/2002 | Kaplan |
| 6,551,303 | B1 | * | 4/2003 | Van Tassel et al. ......... 604/508 |
| 6,561,969 | B2 | * | 5/2003 | Frazier et al. ................ 600/16 |

\* cited by examiner

Primary Examiner—Linda C. M. Dvorak
Assistant Examiner—Ahmed Farah
(74) Attorney, Agent, or Firm—Beck & Tysver, P.L.L.C.

(57) ABSTRACT

The invention describes a method of treating a patient's left atrial appendage through the pericardial space. The process takes place through the pericardial space from an access point outside the pericardium or pericardial space.

4 Claims, 7 Drawing Sheets

ATRIAL APPENDAGE REMODELING DEVICE AND METHOD

FIELD OF THE INVENTION

The present invention relates generally to devices and techniques for remodeling the atrial appendage of a mammal. The process takes place through the pericardial space from an access point outside the pericardium or pericardial space.

BRIEF DESCRIPTION OF THE PRIOR ART

The atrial appendage is an anatomic feature of the left atrium of the human heart. It is widely believed that atrial fibrillation results in a pooling of blood in the atrial appendage which results in clots.

The surgical removal of the atrial appendage through a limited thoracotomy has been proposed by Johnson in U.S. Pat. No. 5,306,234. However, the surgical removal of the appendage remains problematic since the surgical intervention occurs under general anesthesia and is considered major surgery. It should also be realized that even a transluminal minimally invasive approach from inside the heart is problematic since such an approach requires an implantable closure device and has the risk of acute stroke. Typically any closure device left in contact with the interior of the heart is potentially a thrombogenic surface.

For these reasons among others there is a continuing need to improve techniques for occluding or removing the left atrial appendage.

SUMMARY

In contrast to the prior art, the present invention teaches devices and methods of using the devices to remodel the atrial appendage from locations outside the heart but within the pericardial space. In use, the pericardial space is accessed via the chest wall below the rib cage and an endoscope is inserted. It is preferred to perform the process steps under visual guidance although robotic and other location technologies may be used in the alternative. The preferred treatment for the appendage is "wet cautery" where the size and therefore the volume of the appendage is reduced. An alternate preferred device cuts and cauterizes while removing the appendage. Other surgical techniques are useful as well including conventional electrosurgery and cautery and conventional suture and staple techniques. In all instances the volume of the appendage is reduced and in some approaches tissue is removed as well.

BRIEF DESCRIPTION OF THE DRAWINGS

The invention is illustrated in the figures where like reference numeral represent identical structure throughout the several views wherein.

DETAILED DESCRIPTION

Figure 1:
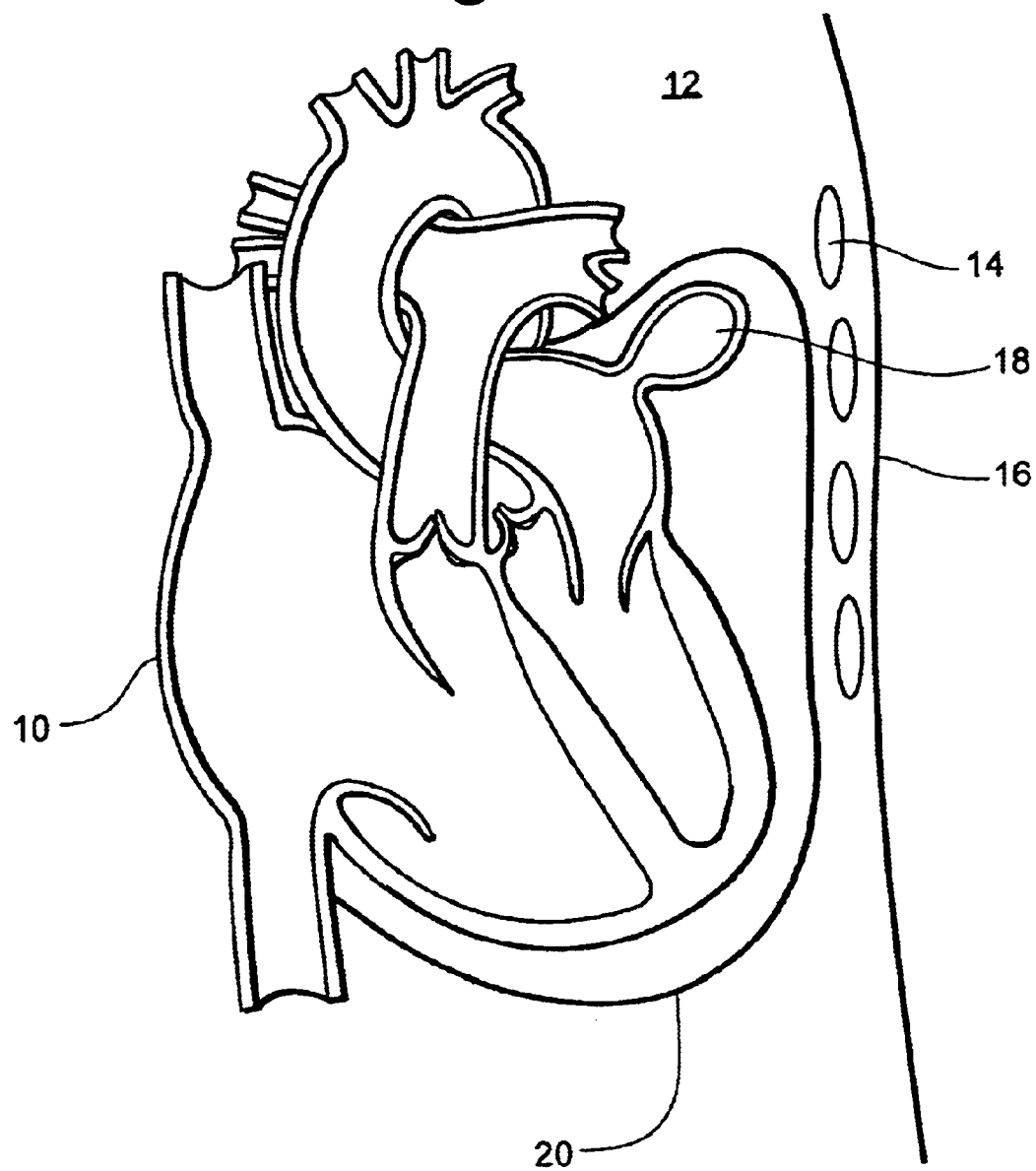
FIG. 1 is a schematic diagram of the patient's chest cavity.

FIG. 1 shows the patients heart 10 located within the patient's chest cavity 12. The ribs 14 and skin 16 show the boundary of the chest cavity 12. The left atrial appendage (LAA) 18 is exaggerated in size to facilitate the description of the invention. The heart 10 chambers lie within the so-called pericardium 20, which is shown in an exaggerated scale. The pericardium 20 is a bag like structure that surrounds the heart. It is attached to the great vessels at the "top" of the heart and it completely encircles the ventricles and the atrium of the heart. The pericardium 20 provides a low friction surface surrounding the heart that permits motion of the heart. In essence the pericardium allows the heart to "beat" without disturbing other near-by organs.

The processes of the invention permit the pericardium to remain "intact". Although several opening to the pericardial space are illustrated it is emphasized that the smaller the number of "holes" in the pericardium are preferred.

Figure 2:
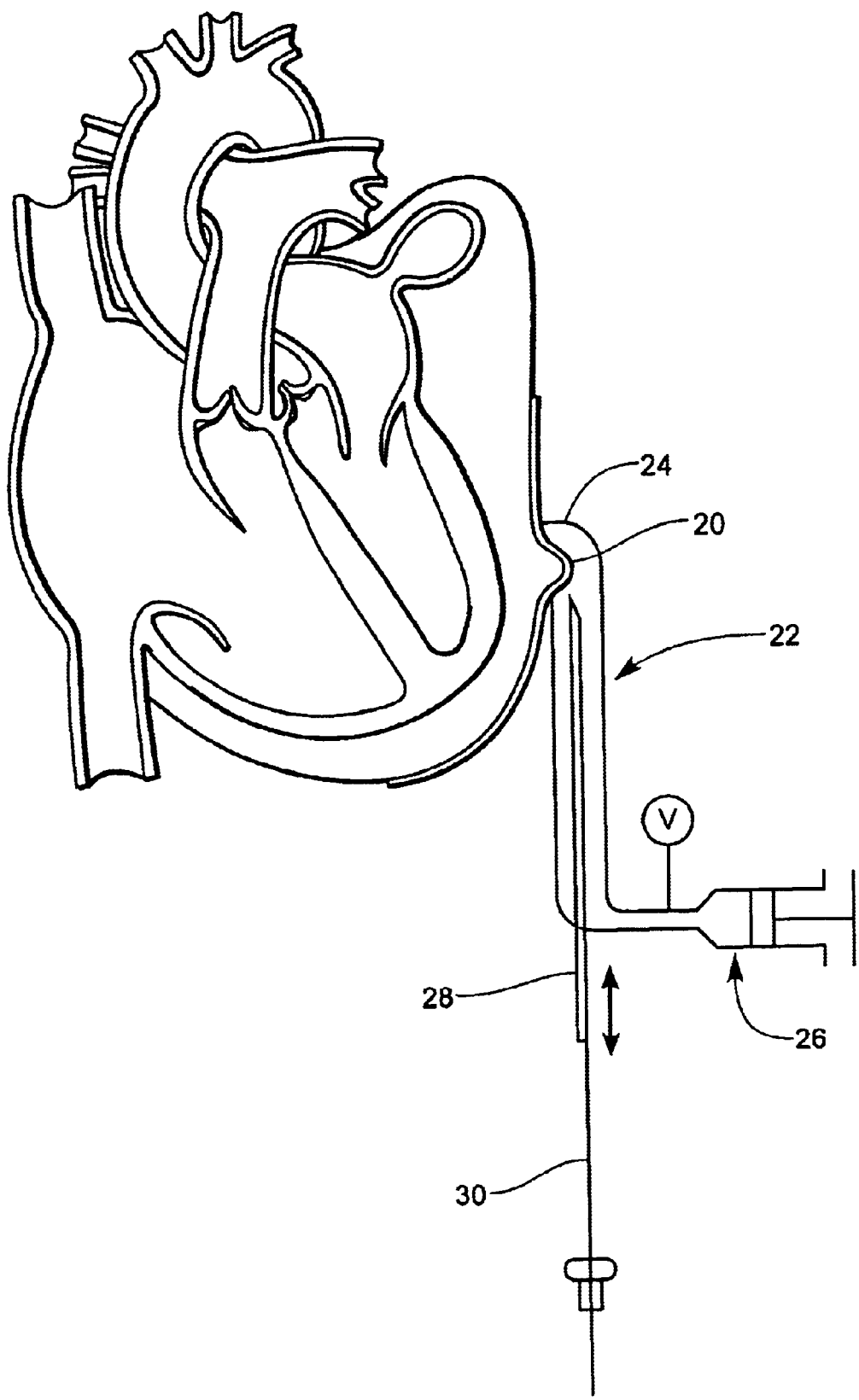
FIG. 2 is a schematic diagram of pericardial access process and device.

FIG. 2 shows initial access to the pericardial space though the use of a pericardial access device 22, which is described in more detail in U.S. Pat. No. 5,827,216 among others. This patent is incorporated by reference herein and the commercially available device is sold under the trademark "Perducer". The Perducer is preferred but alternate devices such as that taught by U.S. Pat. No. 5,931,810 could be freely substituted for the Perducer device. If multiple access points are required for a particular patient the two devices may be used together.

The preferred device 22 has an aperture at its distal end 24 that allows aspiration of the pericardium 20 into the device. An illustrative source of vacuum is shown as the physician operated syringe 26. The aspirated tissue drawn into the device 22 can be pierced by the needle 28. The needle 28 can be translated toward the aspirated tissue by pushing on the proximal end of the needle 28.

A guidewire 30 can next be inserted through the lumen of the needle 28. With the guidewire in the pericardial space, the physician can withdraw the needle and use the guidewire to insert a catheter or other device. The access procedure described may be repeated to provide for multiple access sites or locations into the pericardial space. Although the device shown is preferred it should be recognized that other devices may be used as well.

Figure 3:
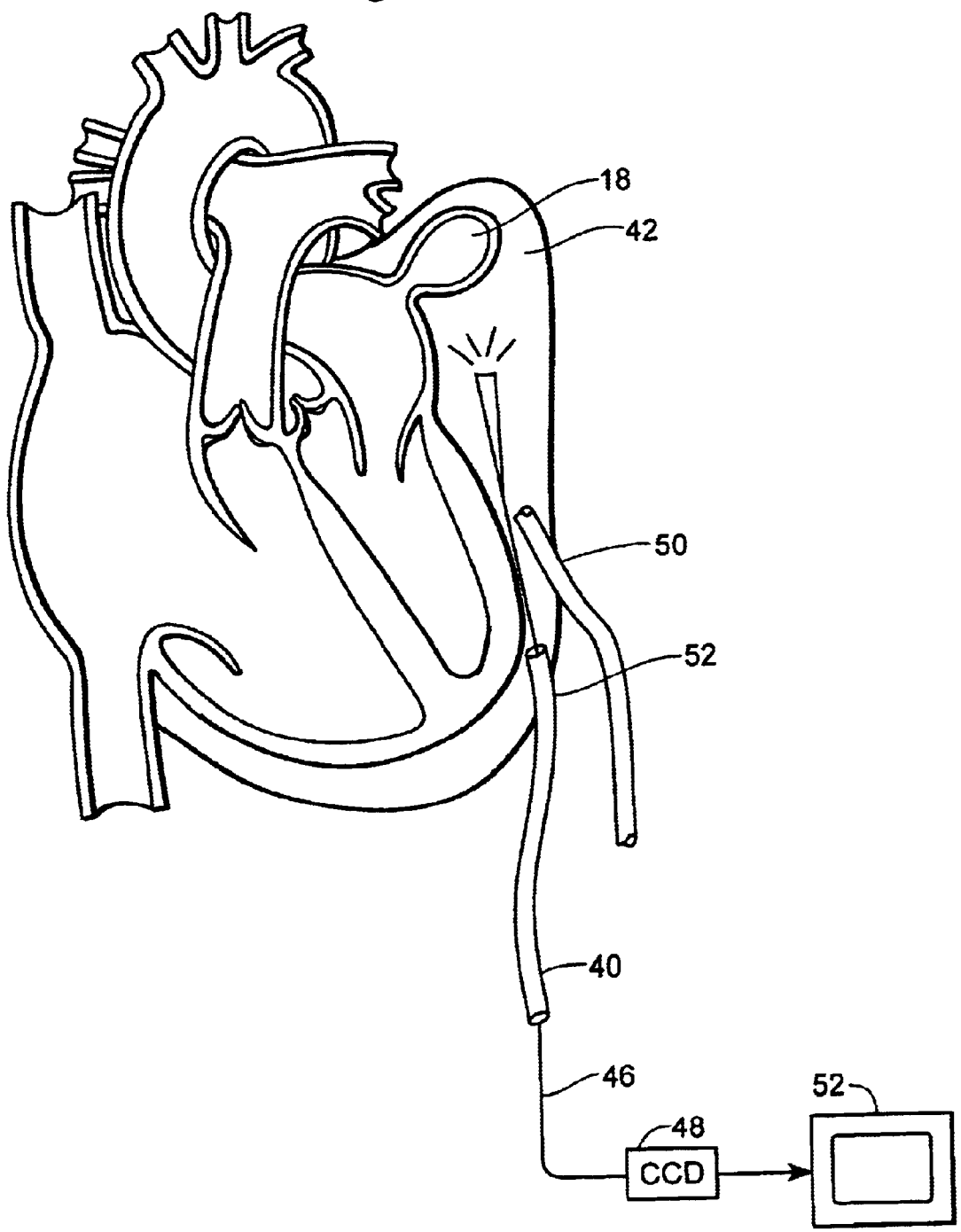
FIG. 3 is a schematic diagram of pericardial space visualization process and device.

FIG. 3 shows two access sites labeled 50 and 52 respectively. A guide catheter 40 has been introduced into the pericardial space 42. This access site or port permits access by the endoscope 46 which includes a camera 48 and a display system 52. Together these devices provide a visualization system allows visual navigation and manipulation of additional surgical tools in the pericardium 20. Although this visualization system is not seen in the remaining drawings its use should be presumed and the deletion from the figure is done to clarify the remaining drawings. It should be noted that most conventional endoscopes in use today have laparoscopic tool access ports built into the device and many steps of the invention can be carried through the scope rather than through a separate access site. However, it is expected that typical atrial appendage reduction would require two sites, with one devoted to the introduction of a endoscope.

Figure 4:
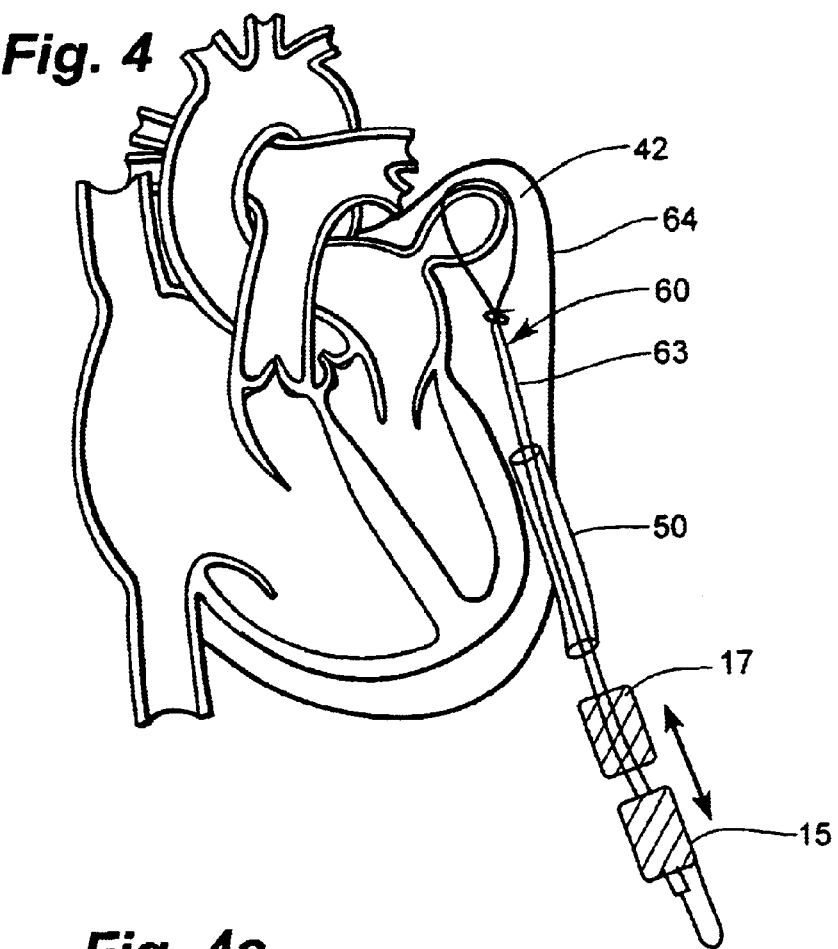
FIG. 4 is a schematic diagram of pericardial space electrocautery process and device.
Figure 4A:
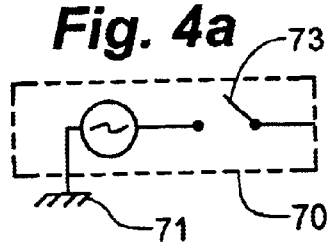

FIG. 4 shows a snare like electrocautery tool 60 introduced into the pericardial space 42. The distal loop 64 has been navigated visually to "lasso" the atrial appendage.

In the device seen in FIG. 4, one end of the snare loop 64 is attached to a tubular body 63 while the other end is carried through the lumen of the tubular body 63 and attached to a sliding handle 15. A fixed handle 17 is attached to the tubular body 63. Traction applied to the snare loop 64 by moving the sliding handle relative to the fixed handle 17 captures the appendage 18. The application of electrical energy (RF) from the electrocautery unit 70 can either remove or close the atrial appendage. It is important to note that this closure process may be essentially bloodless and may be performed under direct visualization through the endoscope (FIG. 3). This process is an example of "dry" cautery as opposed to "wet" cautery described in connection with FIG. 6. Although the snare like device is preferred there are several commercially available products that can also be used for this step including the loop excision electrodes sold by ValleyLab of Colorado. In general, any specific surgeon may prefer to use other familiar tools for the process. Typically, the electrosurgery unit 70 will be connected between the loop 64 and a patient ground depicted as 71. The physician may activate the hand or foot switch 73 to dissect the appendage.

Figure 5:
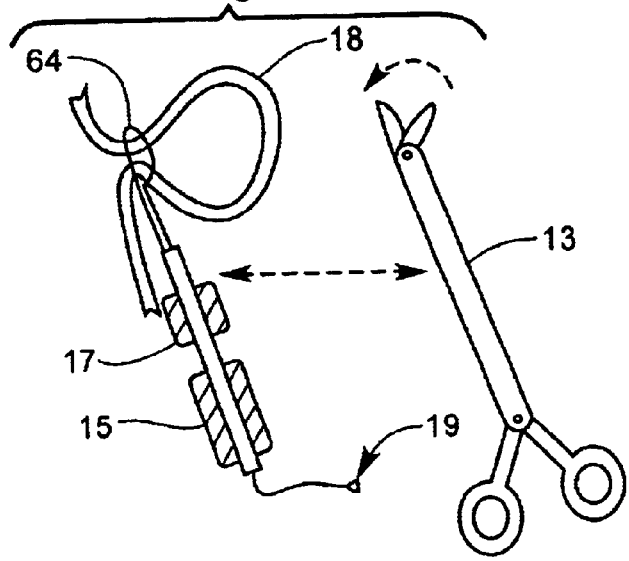
FIG. 5 is a schematic diagram of an electrocautery process and device.

FIG. 5 shows the snare loop 64 isolating the atrial appendage 18 prior to the application of electrical energy. In the figure the physician may grasp an insulator handle and the connection 19 may not be attached to the generator 70 until after the lasso procedure has been accomplished. Although the loop electrocautery device is preferred it should be noted that the conventional unipolar or bipolar cautery scissors such as those illustrated as device 13 may be used to cut off the appendage.

Figure 6:
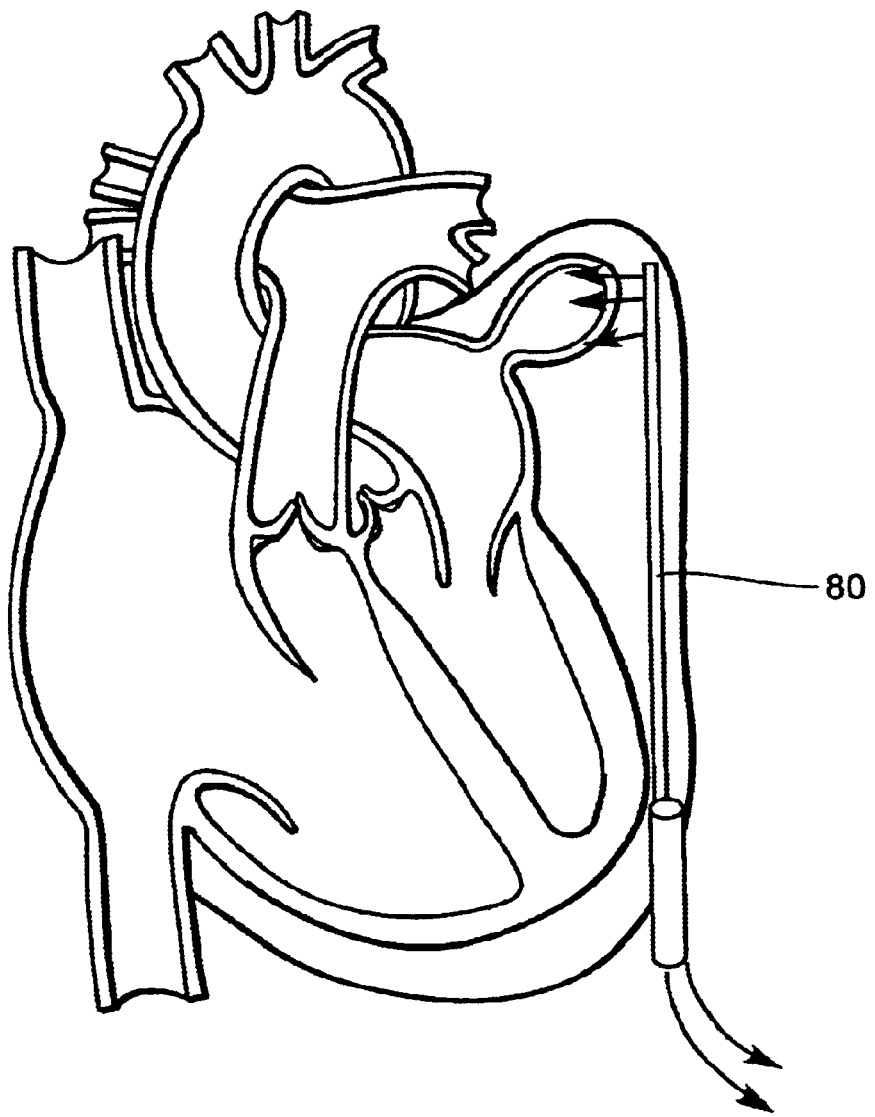
FIG. 6 is a schematic diagram of an electrocautery process and device.
Figure 6A:
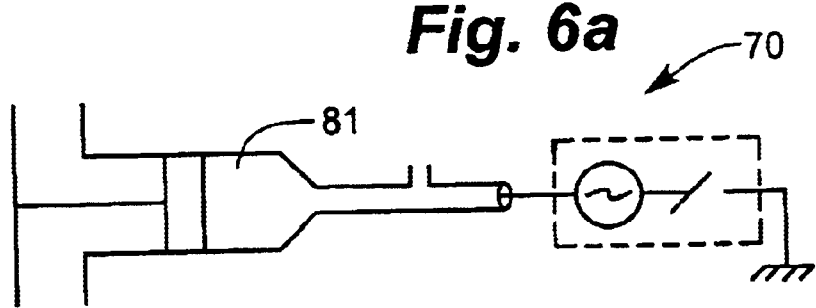

FIG. 6 shows the use of "wet" electrocautery to "reduce" the atrial appendage. In this procedure the electrical catheter 80 is irrigated by a fluid flow of saline or other conductive fluid 81. This wet electrode applies the energy over a wider surface area. As a consequences heat is supplied preferentially to the LAA. It is expected that the application of heat will cause the appendage to reduce in size substantially. Fluid assisted electrocautery is known from U.S. Pat. No. 6,063,081 among others.

Figure 7:
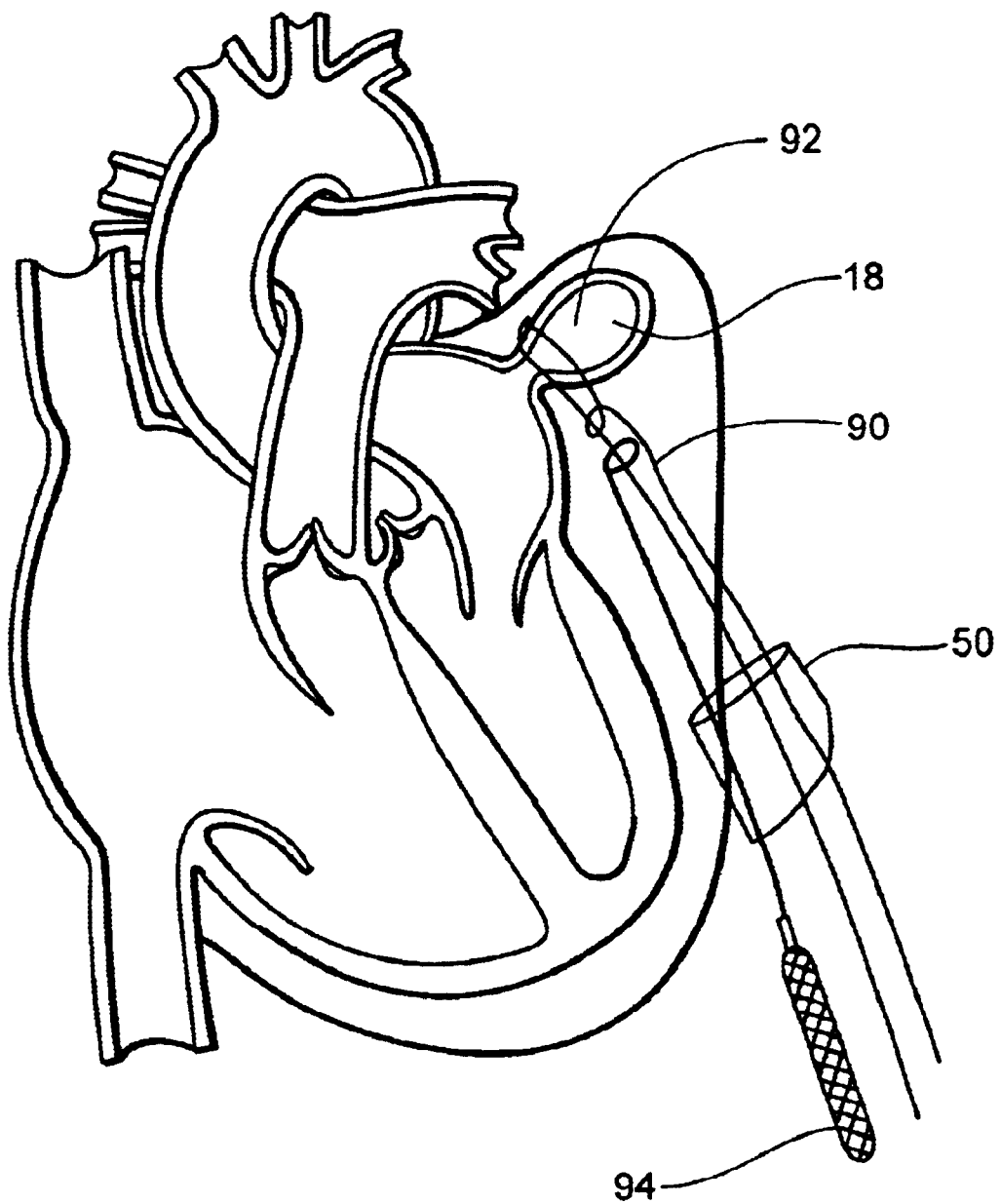
FIG. 7 is a schematic diagram of an endoscopic suture placement process.

FIG. 7 shows an alternate method of closing off the atrial appendage. In this situation a suture 90 has been formed into a loop 92 and passed over the atrial appendage. A laparoscopic knot pusher 94 is passed down one leg of the suture 90 to place and tighten a knot formed in the suture. The use of a suture may be preferred given the size and shape of the appendage 18.

Figure 8:
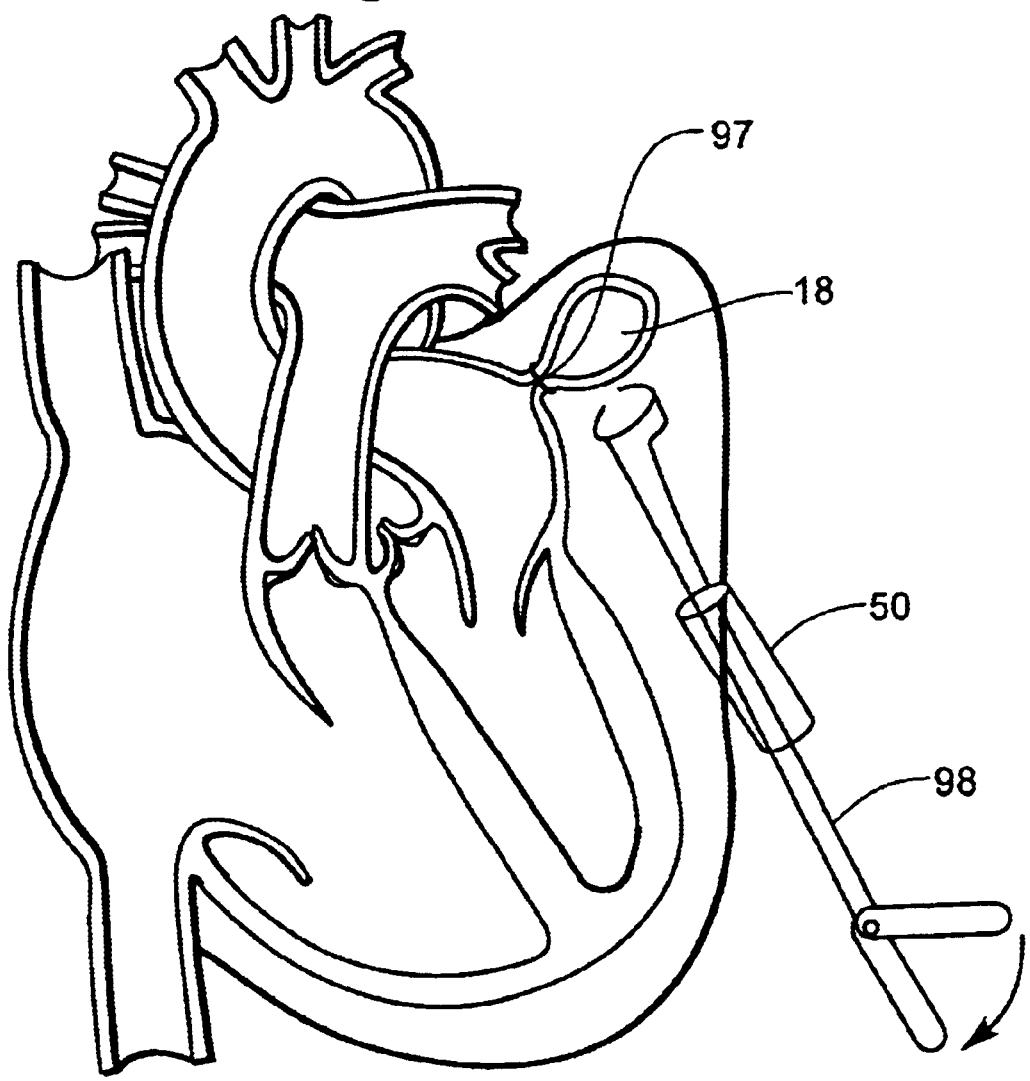
FIG. 8 is a schematic diagram of an endoscopic staple placement process.

FIG. 8 illustrates an alternate closure device and process. In this figure a laparoscopic stapler is used to place one or more staples to close off the atrial appendage. In the figure the tool 98 has been used to place one staple seen as staple 97 closing off the appendage.

What is claimed is:

1. A method for treating the atrial appendage comprising:
   entering the chest cavity with a surgical instrument creating a surgical opening;
   introducing a pericardial access device through said opening;
   entering the pericardial space between the pericardium and the heart at a location remote from the atrial appendage;
   navigating an endoscopic suturing device to the atrial appendage whereby said endoscopic suturing device remains between the endocardial surface and the intact pericardial surface at the site of the atrial appendage;
   activating the suturing device to ensnare the atrial appendage with a suture, thereby closing off the atrial appendage;
   introducing a knot pusher along said suture into the pericardial space to tighten said suture;
   removing both the endoscopic suturing device and the knot pusher.

2. The method of claim 1 wherein the pericardial access device includes a vacuum source for creating a bleb of pericardial tissue at the entry site.

3. The method of claim 2 wherein the pericardial access device includes a needle to piece said bleb of pericardial tissue at the entry site.

4. The method of claim 1 further including an endoscpoic visualization device located proximate said atrial appendage, delivered between said pericardium and said endocardial surface.

* * * * *